US009820681B2

(12) United States Patent
Baker, Jr.

(10) Patent No.: US 9,820,681 B2
(45) Date of Patent: Nov. 21, 2017

(54) REDUCING NUISANCE ALARMS

(71) Applicant: Covidien LP, Boulder, CO (US)

(72) Inventor: Clark R. Baker, Jr., Newman, CA (US)

(73) Assignee: Covidien LP, Mansfield, MA (US)

(*) Notice: Subject to any disclaimer, the term of this patent is extended or adjusted under 35 U.S.C. 154(b) by 170 days.

(21) Appl. No.: 14/315,693

(22) Filed: Jun. 26, 2014

(65) Prior Publication Data

US 2014/0309507 A1   Oct. 16, 2014

Related U.S. Application Data

(63) Continuation of application No. 12/399,304, filed on Mar. 6, 2009, now Pat. No. 8,792,949.

(60) Provisional application No. 61/041,042, filed on Mar. 31, 2008.

(51) Int. Cl.
   *A61B 5/1455*   (2006.01)
   *A61B 5/00*     (2006.01)
   *G06F 19/00*    (2011.01)

(52) U.S. Cl.
   CPC ...... *A61B 5/14552* (2013.01); *A61B 5/14551* (2013.01); *A61B 5/7221* (2013.01); *G06F 19/3406* (2013.01); *A61B 5/746* (2013.01); *G06F 19/3418* (2013.01)

(58) Field of Classification Search
   CPC .................................................. A61B 5/14551
   USPC ......................................................... 600/323
   See application file for complete search history.

(56) References Cited

U.S. PATENT DOCUMENTS

| | | | |
|---|---|---|---|
| 4,714,341 A * | 12/1987 | Hamaguri | A61B 5/14551 356/41 |
| 4,752,089 A | 6/1988 | Carter | |
| 4,863,265 A | 9/1989 | Flower et al. | |
| 4,921,642 A | 5/1990 | LaTorraca | |
| 4,954,799 A | 9/1990 | Kumar | |
| 5,057,822 A | 10/1991 | Hoffman | |
| 5,072,737 A | 12/1991 | Goulding | |
| 5,150,291 A | 9/1992 | Cummings et al. | |
| 5,161,525 A | 11/1992 | Kimm et al. | |
| 5,199,439 A * | 4/1993 | Zimmerman | A61B 5/00 600/483 |
| 5,237,987 A | 8/1993 | Anderson et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |

(Continued)

OTHER PUBLICATIONS

7200 Series Ventilator, Options, and Accessories: Operators Manual. Nellcor Puritan Bennett, Part No. 22300 A, Sep. 1990, pp. 1-196.

(Continued)

*Primary Examiner* — Michael C Stout
*Assistant Examiner* — Nicholas E Kolderman
(74) *Attorney, Agent, or Firm* — Merchant & Gould P.C.

(57) ABSTRACT

Embodiments disclosed herein may describe systems and methods for reducing nuisance alarms using probability and/or accuracy of a measured physiological parameter, such as the pulse rate or SpO2 measurement generated by a pulse oximeter. Embodiments may include methods for adjusting a predetermined alarm threshold based on the probability distribution of the estimated pulse rate and/or oxygen saturation of a patient's blood.

7 Claims, 9 Drawing Sheets

(56) References Cited

U.S. PATENT DOCUMENTS

| | | |
|---|---|---|
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brady |
| 5,544,674 A | 8/1996 | Kelly |
| 5,549,106 A | 8/1996 | Gruenke et al. |
| 5,596,984 A | 1/1997 | O'Mahoney et al. |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,853,364 A * | 12/1998 | Baker, Jr. ........... A61B 5/02416 367/155 |
| 5,864,938 A | 2/1999 | Gansel et al. |
| 5,865,168 A | 2/1999 | Isaza |
| 5,865,736 A | 2/1999 | Baker et al. |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,161,539 A | 12/2000 | Winter |
| 6,220,245 B1 | 4/2001 | Takabayashi et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,358,213 B1 | 3/2002 | Friedman et al. |
| 6,360,745 B1 | 3/2002 | Wallace et al. |
| 6,369,838 B1 | 4/2002 | Wallace et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,622,726 B1 | 9/2003 | Du |
| 6,644,310 B1 | 11/2003 | Delache et al. |
| 6,668,824 B1 | 12/2003 | Isaza et al. |
| 6,675,031 B1 | 1/2004 | Porges et al. |
| 6,675,801 B2 | 1/2004 | Wallace et al. |
| 6,684,090 B2 | 1/2004 | Ali et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,814,074 B1 | 11/2004 | Nadjafizadeh et al. |
| 6,836,679 B2 | 12/2004 | Baker, Jr. et al. |
| 6,866,040 B1 | 3/2005 | Bourdon |
| 6,960,854 B2 | 11/2005 | Nadjafizadeh et al. |
| 7,036,504 B2 | 5/2006 | Wallace et al. |
| 7,077,131 B2 | 7/2006 | Hansen |
| RE39,225 E | 8/2006 | Isaza et al. |
| 7,117,438 B2 | 10/2006 | Wallace et al. |
| 7,270,126 B2 | 9/2007 | Wallace et al. |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,487,773 B2 | 2/2009 | Li |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,792,949 B2 | 7/2014 | Baker, Jr. |
| 2002/0035315 A1* | 3/2002 | Ali ................... A61B 5/1455 600/300 |
| 2004/0138540 A1 | 7/2004 | Baker et al. |
| 2005/0039748 A1 | 2/2005 | Andrieux |
| 2005/0139212 A1 | 6/2005 | Bourdon |
| 2007/0017515 A1 | 1/2007 | Wallace et al. |
| 2007/0077200 A1 | 4/2007 | Baker |

(56) References Cited

U.S. PATENT DOCUMENTS

| | | |
|---|---|---|
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0033254 A1* | 2/2008 | Kamath ............. A61B 5/14532 600/300 |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0076986 A1* | 3/2008 | Pav ................... A61B 5/14551 600/323 |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |
| 2013/0284177 A1 | 10/2013 | Li et al. |

(56) References Cited

U.S. PATENT DOCUMENTS

2014/0000606 A1    1/2014   Doyle et al.
2014/0012150 A1    1/2014   Milne et al.
2014/0034054 A1    2/2014   Angelico et al.

OTHER PUBLICATIONS

7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operators and Technical Reference Manual. Ventilator System, Nellcor Puritan Bennett, Part No. 4-075609-00, Rev. G, Oct. 2006, pp. 1-424.

\* cited by examiner

REDUCING NUISANCE ALARMS

RELATED APPLICATIONS

This application is a continuation application of U.S. patent application Ser. No. 12/399,304, filed Mar. 6, 2009 (now U.S. Pat. No. 8,792,949), which application claims priority to U.S. Provisional Application No. 61/041,042, filed Mar. 31, 2008, the complete disclosures of which are hereby incorporated by reference in their entirety.

BACKGROUND

In medicine, a plethysmograph is an instrument that measures physiological parameters, such as variations in the size of an organ or body part, through an analysis of the blood passing through or present in the targeted body part, or a depiction of these variations. An oximeter is an instrument that determines the oxygen saturation of the blood. One common type of oximeter is a pulse oximeter, which determines oxygen saturation by analysis of an optically sensed plethysmograph.

A pulse oximeter is a medical device that indirectly measures the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient.

A pulse oximeter typically includes a light sensor that is placed at a site on a patient, usually a fingertip, toe, forehead or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths at different points in the pulse cycle, it is possible to estimate the blood oxygen saturation of hemoglobin in arterial blood. This relies on the observation that highly oxygenated blood will absorb relatively more red light and less infrared light than blood with lower oxygen saturation.

SUMMARY

This disclosure describes systems and methods for reducing nuisance alarms using probability and/or accuracy of a measured physiological parameter, such as the SpO2 and/or pulse rate measurement generated by a pulse oximeter. As discussed in greater detail below, the disclosure describes methods for adjusting a predetermined alarm threshold based on the probability distribution of the estimated oxygen saturation of a patient's blood and further describes methods for delaying signaling an alarm based on the accuracy of the estimated oxygen saturation. In one aspect, the disclosure describes a method for generating an alarm indicating that a physiological parameter has exceeded a predetermined threshold. The method includes calculating a probability distribution of an actual value of the physiological parameter based on data received from a sensor or detector. The method then identifies the predetermined threshold associated with the physiological parameter and generates the alarm based on the predetermined threshold and the probability distribution.

In another aspect, the disclosure describes another method for generating an alarm indicating that a physiological parameter has exceeded a predetermined threshold. The method includes calculating a first estimated value of the physiological parameter and a first accuracy of the first estimated value from data. The method then determines that the first estimated value of the physiological parameter exceeds the predetermined threshold. However, instead of generating an alarm immediately, the method delays generating the alarm based on the first accuracy. The first accuracy is used to calculate a delay period after which, if the physiological parameter still exceeds the predetermined threshold, the alarm is generated.

In yet another aspect, the disclosure describes a pulse oximeter that includes an oxygen saturation module capable of calculating an estimated value of oxygen saturation of a patient's blood from information received from a sensor; an accuracy module capable of calculating the accuracy of the estimated value; and an alarm module capable of generating an alarm based on the estimated value and a predetermined alarm threshold, wherein the alarm module is capable of delaying the generation of an alarm based on the accuracy of the estimated value. The pulse oximeter may also include a probability distribution module capable of calculating a probability distribution of an actual value of the oxygen saturation of a patient's blood from information received from the sensor. In this embodiment, the alarm module is further capable of calculating an adjusted threshold based on the probability distribution and the predetermined threshold and generating an alarm based on the adjusted threshold.

The disclosure also describes a combined method for generating an alarm in which an adjusted threshold is calculated and if that threshold is exceeded, a delay period may be used to delay the generation of an alarm. For example, an embodiment of such a combined method includes the operations: a) receiving current data indicative of the physiological parameter; b) calculating an estimated value of the physiological parameter and an accuracy of the estimated value based on the current data; c) calculating a probability distribution of an actual value of the physiological parameter based on the current data; d) calculating an adjusted threshold based on the predetermined threshold and the probability distribution; e) determining that the estimated value of the physiological parameter exceeds the adjusted threshold; and f) delaying generating the alarm for at least a first time period based on a comparison of the accuracy with a predetermined accuracy range. After delaying generating the alarm for at least a first time period, operations a), b) and e) may be repeated and the alarm then generated. Alternatively, operations a)-e) may be repeated.

These and various other features as well as advantages which characterize the disclosed systems and methods will be apparent from a reading of the following detailed description and a review of the associated drawings. Additional features of the systems and methods described herein are set forth in the description which follows, and in part will be apparent from the description, or may be learned by practice of the technology. The benefits and features will be realized and attained by the structure particularly pointed out in the written description and claims as well as the appended drawings.

It is to be understood that both the foregoing general description and the following detailed description are exemplary and explanatory and are intended to provide further explanation of the disclosed technology as claimed.

BRIEF DESCRIPTION OF THE DRAWINGS

The following drawing figures, which form a part of this application, are illustrative of disclosed technology and are not meant to limit the scope of the description in any manner, which scope shall be based on the claims appended hereto.

DETAILED DESCRIPTION

This disclosure describes systems and methods for reducing nuisance alarms using probability and/or accuracy of a measured physiological parameter, such as the SpO2 and/or pulse rate measurements generated by a pulse oximeter. As discussed in greater detail below, the disclosure describes methods for adjusting a predetermined alarm threshold based on the probability distribution of the estimated oxygen saturation of a patient's blood and further describes methods for delaying signaling an alarm based on the accuracy of the estimated oxygen saturation.

Although the techniques for generating alarms based on an estimated physiological parameter introduced above and discussed in detail below may be implemented by a variety of medical devices and for a variety of physiological parameters, the present disclosure will discuss the implementation of these techniques in a pulse oximeter. Although described in detail in this context of a pulse oximeter displaying oxygen saturation measurements, the reader will understand that the systems and methods described herein may be equally adapted to the generation of alarms based on the measurement of any physiological parameter of any patient (human or non-human) generated by any monitoring device.

Figure 1:
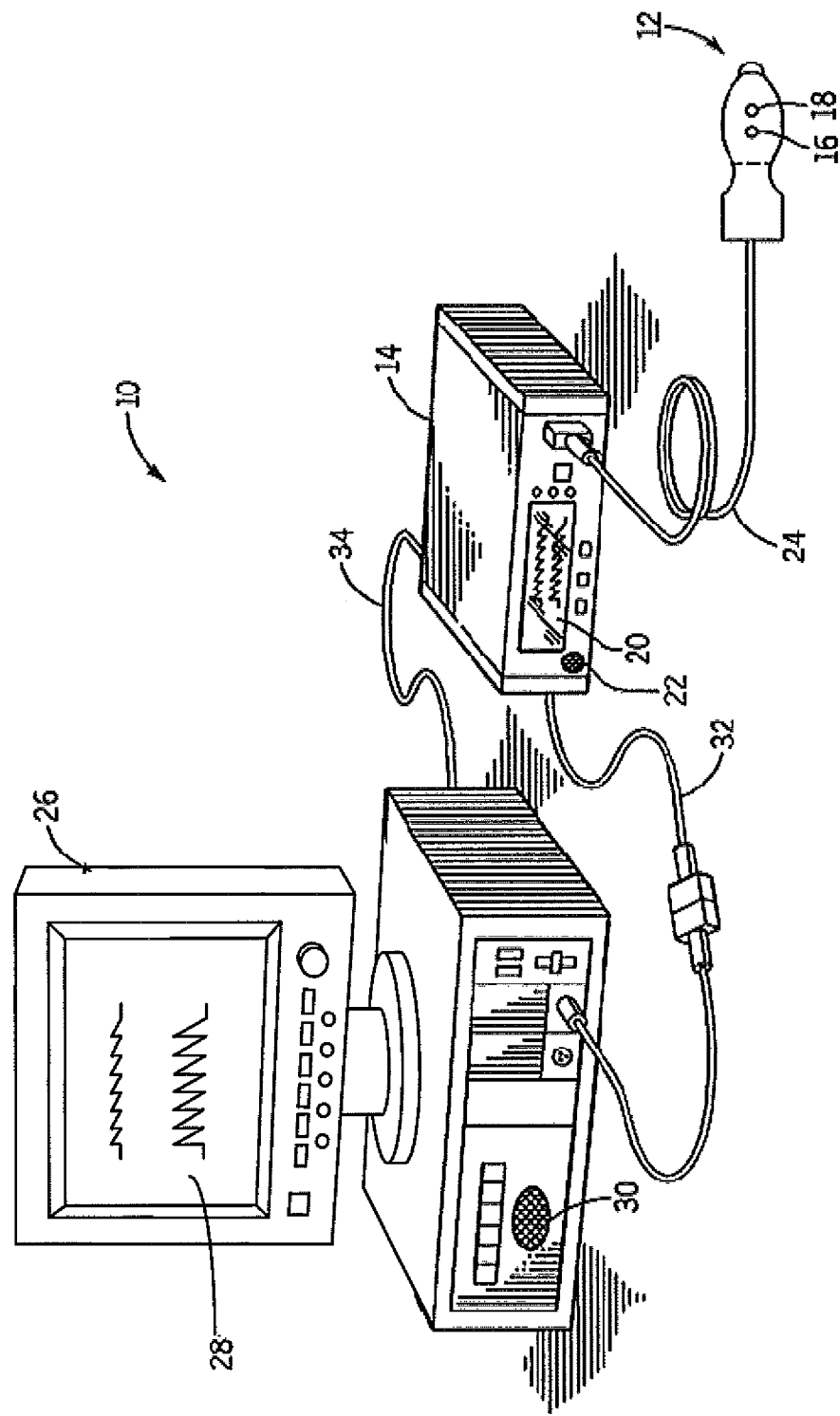
FIG. 1 is a perspective view of a pulse oximetry system, according to an embodiment.

FIG. 1 is a perspective view of an embodiment of a pulse oximetry system 10. The system 10 includes a sensor 12 and a pulse oximetry monitor 14. The sensor 12 includes an emitter 16 for emitting light at one or more wavelengths into a patient's tissue. A detector 18 is also provided in the sensor 12 for detecting the light originally from the emitter 16 that emanates from the patient's tissue after passing through the tissue. The emitter 16 and detector 18 may be on opposite sides of a digit such as a finger or toe, in which case the light that is emanating from the tissue has passed completely through the digit. In an alternative embodiment, the emitter 16 and detector 18 may be arranged so that light from the emitter 16 penetrates the tissue and is reflected by the tissue into the detector 18, such as a sensor designed to obtain pulse oximetry data from a patient's forehead.

The sensor may be connected to and draw its power from the monitor 14 as shown. Alternatively, the sensor may be wirelessly connected to the monitor 14 and include its own battery or similar power supply (not shown). The monitor 14 may be configured to calculate physiological parameters based on data received from the sensor 12 relating to light emission and detection. Further, the monitor 14 includes a display 20 configured to display the physiological parameters, other information about the system, and/or alarm indications. In the embodiment shown, the monitor 14 also includes a speaker 22 to provide an audible alarm in the event that the patient's physiological parameters are not within a normal range, as defined based on patient characteristics.

The sensor 12 is communicatively coupled to the monitor 14 via a cable 24. However, in other embodiments a wireless transmission device (not shown) or the like may be utilized instead of or in addition to the cable 24.

In the illustrated embodiment, the pulse oximetry system 10 also includes a multi-parameter patient monitor 26. The monitor may be cathode ray tube type, a flat panel display (as shown) such as a liquid crystal display (LCD) or a plasma display, or any other type of monitor now know or later developed. The multi-parameter patient monitor 26 may be configured to calculate physiological parameters and to provide a central display 28 for information from the monitor 14 and from other medical monitoring devices or systems (not shown). For example, the multiparameter patient monitor 26 may be configured to display an estimate of a patient's blood oxygen saturation generated by the pulse oximetry monitor 14 (referred to as an "$SpO_2$"), pulse rate information from the monitor 14 and blood pressure from a blood pressure monitor (not shown) on the display 28. Additionally, the multi-parameter patient monitor 26 may emit a visible or audible alarm via the display 28 or a speaker 30, respectively, if the patient's physiological parameters are found to be outside of the normal range. The monitor 14 may be communicatively coupled to the multi-parameter patient monitor 26 via a cable 32 or 34 coupled to a sensor input port or a digital communications port, respectively or may communicate wirelessly (not shown). In addition, the monitor 14 and/or the multi-parameter patient monitor 26 may be connected to a network to enable the sharing of information with servers or other workstations (not shown). The monitor 14 may be powered by a battery (not shown) or by a conventional power source such as a wall outlet.

Figure 2:
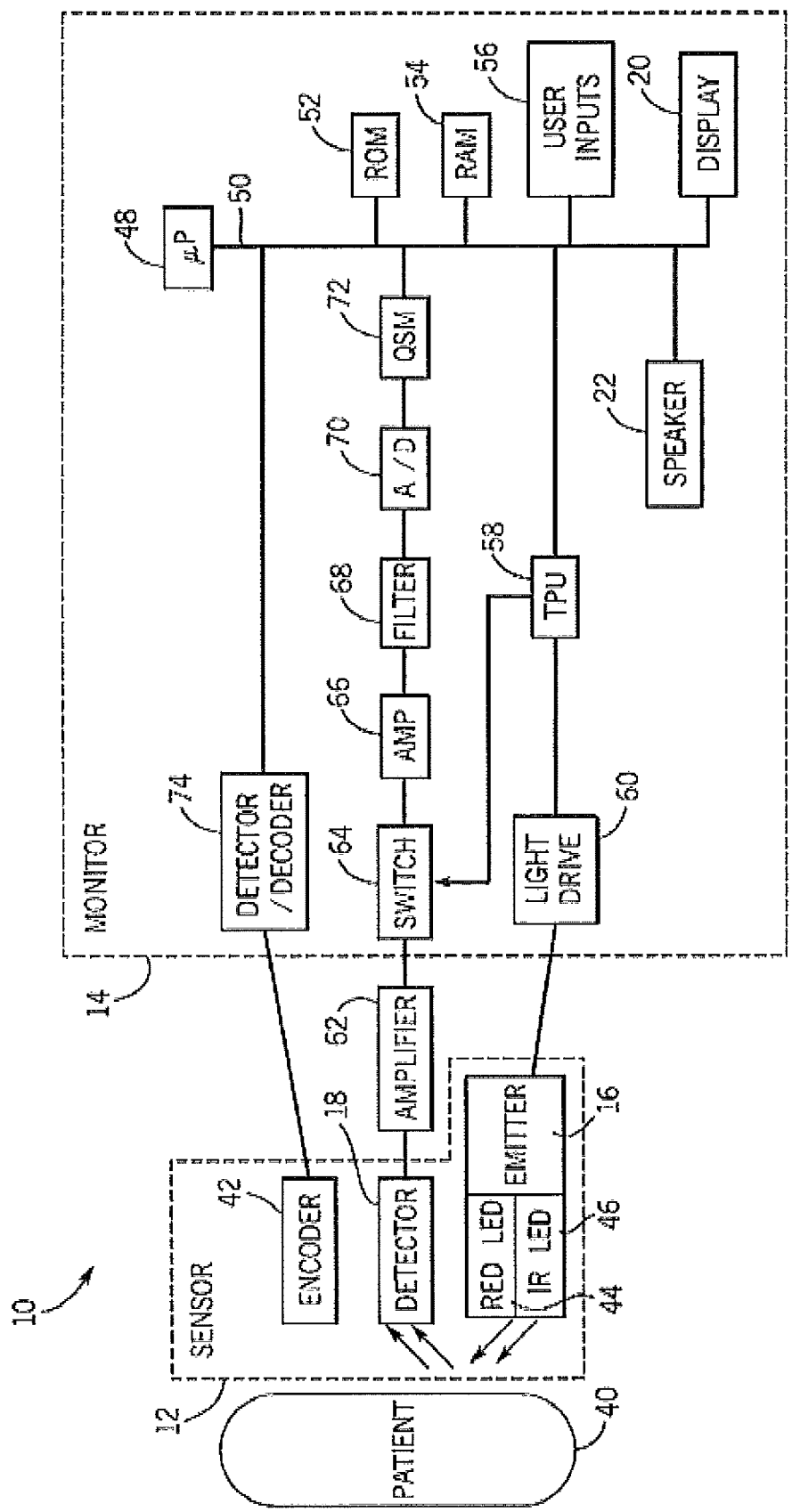
FIG. 2 is a block diagram of the exemplary pulse oximetry system of FIG. 1 coupled to a patient, according to an embodiment.

FIG. 2 is a block diagram of the embodiment of a pulse oximetry system 10 of FIG. 1 coupled to a patient 40 in accordance with present embodiments. Specifically, certain components of the sensor 12 and the monitor 14 are illustrated in FIG. 2. The sensor 12 includes the emitter 16, the detector 18, and an encoder 42. In the embodiment shown, the emitter 16 is configured to emit at least two wavelengths of light, e.g., RED and IR, into a patient's tissue 40. Hence, the emitter 16 may include a RED light emitting light source such as the RED light emitting diode (LED) 44 shown and an IR light emitting light source such as the IR LED 46 shown for emitting light into the patient's tissue 40 at the wavelengths used to calculate the patient's physiological parameters. In certain embodiments, the RED wavelength may be generally between about 600 nm and about 700 nm, and the IR wavelength may be between about 800 nm and about 1000 nm.

Alternative light sources may be used in other embodiments. For example, a single wide-spectrum light source may be used, and the detector 18 may be configured to detect light only at certain wavelengths. Alternatively, a third light source may be provided based on its ability to obtain an accurate signal when the starting oxygen saturation is known while consuming less power. In another example, the detector 18 may detect a wide spectrum of wavelengths of light, and the monitor 14 may process only those wavelengths which are of interest or which take the least power to detect.

It should be understood that, as used herein, the term "light" may refer to one or more of ultrasound, radio, microwave, millimeter wave, infrared, visible, ultraviolet, gamma ray, X-ray and/or other electromagnetic radiation, and may also include any wavelength within the radio, microwave, infrared, visible, ultraviolet, or X-ray spectra, and that any suitable wavelength of light may be appropriate for use with the present techniques.

In an embodiment, the detector 18 may be configured to detect the intensity of light at the RED and IR wavelengths. In operation, light enters the detector 18 after passing through the patient's tissue 40. The detector 18 converts the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, the detector 18 sends the signal to the monitor 14, where physiological parameters may be calculated based on the absorption of the RED and IR wavelengths in the patient's tissue 40. An examples of devices configured to perform such calculations are the Model N600 and N600x pulse oximeters available from Nellcor Puritan Bennett LLC.

In an embodiment, the encoder 42 may contain information about the sensor 12, such as what type of sensor it is (e.g., whether the sensor is intended for placement on a forehead or digit) and the wavelengths of light emitted by the emitter 16. This information may be used by the monitor 14 to select appropriate algorithms, lookup tables and/or calibration coefficients stored in the monitor 14 for calculating the patient's physiological parameters. In addition the encoder 42 may include information such as coefficients utilized for the calculation of SpO2. All information in the encoder 42 may be digitally encoded to insure accuracy, among other considerations.

In addition, the encoder 42 may contain information specific to the patient 40, such as, for example, the patient's age, weight, and diagnosis. This information may allow the monitor 14 to determine patient-specific threshold ranges in which the patient's physiological parameter measurements should fall and to enable or disable additional physiological parameter algorithms. The encoder 42 may, for instance, be a coded resistor which stores values corresponding to the type of the sensor 12, the wavelengths of light emitted by the emitter 16, and/or the patient's characteristics. These coded values may be communicated to the monitor 14, which determines how to calculate the patient's physiological parameters and alarm threshold ranges. In another embodiment, the encoder 42 may include a memory on which one or more of the following information may be stored for communication to the monitor 14: the type of the sensor 12; the wavelengths of light emitted by the emitter 16; the proper calibration coefficients and/or algorithms to be used for calculating the patient's physiological parameters and/or alarm threshold values; the patient characteristics to be used for calculating the alarm threshold values; and the patient-specific threshold values to be used for monitoring the physiological parameters.

Signals from the detector 18 and the encoder 42 may be transmitted to the monitor 14. In the embodiment shown, the monitor 14 includes a general-purpose microprocessor 48 connected to an internal bus 50. The microprocessor 48 is adapted to execute software, which may include an operating system and one or more applications, as part of performing the functions described herein. Also connected to the bus 50 are a read-only memory (ROM) 52, a random access memory (RAM) 54, user inputs 56, the display 20, and the speaker 22.

The RAM 54 and ROM 52 are illustrated by way of example, and not limitation. Any computer-readable media may be used in the system for data storage. Computer-readable media are capable of storing information that can be interpreted by the microprocessor 48. This information may be data or may take the form of computer-executable instructions, such as software applications, that cause the microprocessor to perform certain functions and/or computer-implemented methods. Depending on the embodiment, such computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 provides timing control signals to a light drive circuitry 60 which controls when the emitter 16 is illuminated and multiplexed timing for the RED LED 44 and the IR LED 46. The TPU 58 also controls the gating-in of signals from detector 18 through an amplifier 62 and a switching circuit 64. These signals are sampled at the proper time, depending upon which light source is illuminated. The received signal from the detector 18 may be passed through an amplifier 66, a low pass filter 68, and an analog-to-digital converter 70. The digital data may then be stored in a queued serial module (QSM) 72 (or buffer) for later downloading to the RAM 54 as the QSM 72 fills up. In one embodiment, there may be multiple separate parallel paths having the amplifier 66, the filter 68, and the A/D converter 70 for multiple light wavelengths or spectra received.

The microprocessor 48 may determine the patient's physiological parameters, such as $SpO_2$ and pulse rate, using various algorithms and/or look-up tables based on the value of the received signals and/or data corresponding to the light received by the detector 18. Signals corresponding to information about the patient 40, and particularly about the intensity of light emanating from a patient's tissue over time, may be transmitted from the encoder 42 to a decoder 74. These signals may include, for example, encoded information relating to patient characteristics. The decoder 74 may translate these signals to enable the microprocessor to determine the thresholds based on algorithms or look-up tables stored in the ROM 52. The encoder 42 may also contain the patient-specific alarm thresholds, for example, if the alarm values are determined on a workstation separate from the monitor 14. The user inputs 56 may also be used to enter information about the patient, such as age, weight, height, diagnosis, medications, treatments, and so forth. In certain embodiments, the display 20 may exhibit a list of values which may generally apply to the patient, such as, for example, age ranges or medication families, which the user may select using the user inputs 56. The microprocessor 48 may then determine the proper thresholds using the user input data and algorithms stored in the ROM 52. The patient-specific thresholds may be stored on the RAM 54 for comparison to measured physiological parameters.

The embodiments described herein relate to adjusting the conditions under which an alarm is generated based on one or more statistical parameters of an estimated physiological parameter value. Statistical parameters associated with the physiological parameter include parameters related to the accuracy of the estimated value such as error estimates and probability distributions of the data.

Figure 3:
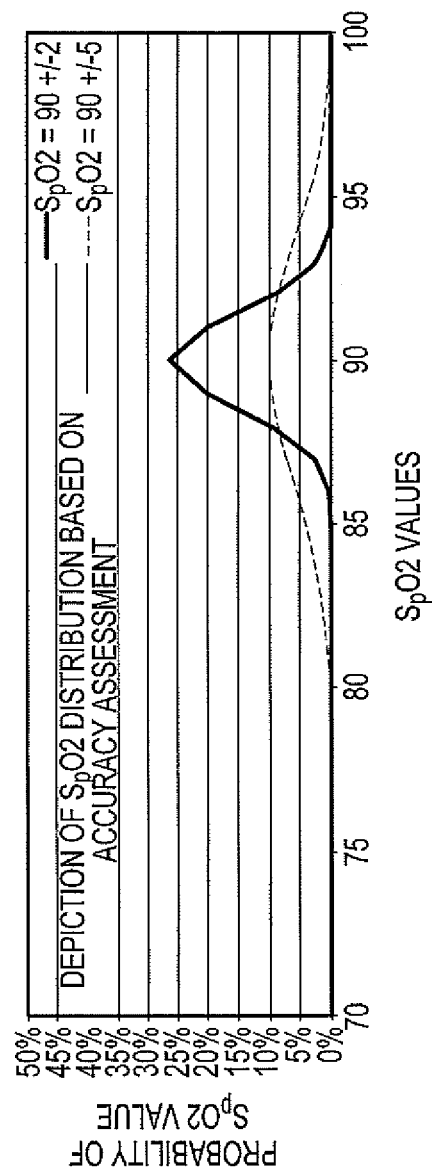
FIG. 3 shows a depiction of two Gaussian bell-curves of the probability distribution in which the estimated $SpO_2$ value is 90%, but having accuracies of +/−2 (solid) and +/−5 (dashed) respectively, according to an embodiment.
Figure 4:
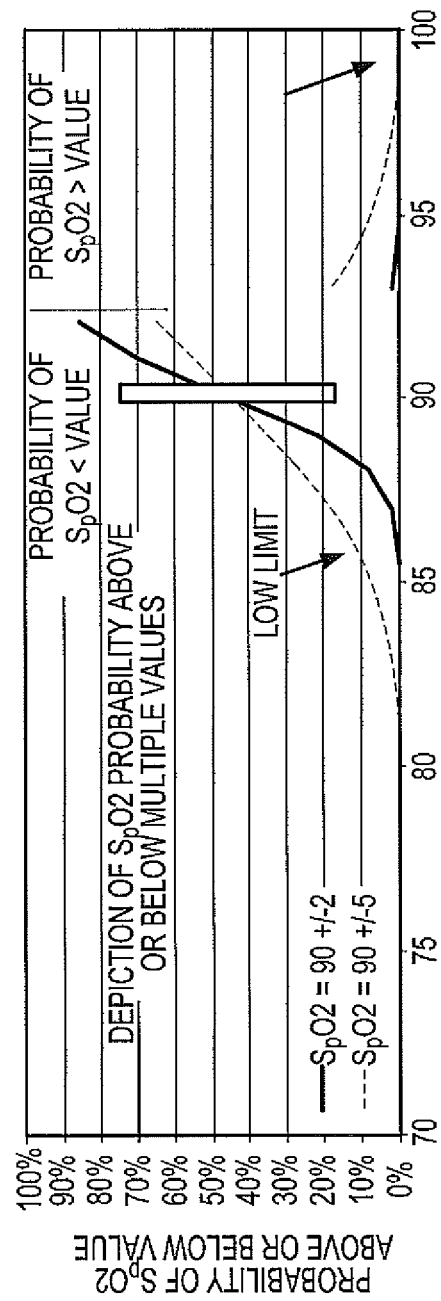
FIG. 4 depicts the same distributions as shown in FIG. 4 plotted as the cumulative probability that the actual $SpO_2$ value is below or above each of the $SpO_2$ values on x-axis, according to an embodiment.

The following FIGS. 3 and 4 illustrate how different accuracies of estimates of $SpO_2$ values affect the probability distribution of the estimated values, according to various embodiments. FIG. 3 shows a depiction of two Gaussian bell-curves of the probability distribution in which the estimated $SpO_2$ value is 90%, but having accuracies of +/−2% (solid) and +/−5% (dashed) respectively. As shown in FIG. 3, the difference in accuracy has a large effect on the probability distribution and the probability that the actual $SpO_2$ value is above or below any particular value. For example, if the accuracy is +1-2%, there is nearly a 100% chance that the actual value of the $SpO_2$ value is within the interval of 85% to 95%. The same can not be said of the data having an accuracy of +/−5%.

FIG. 4 depicts the same two contrasting examples, but shows the cumulative probability that the actual $SpO_2$ value is below or above each of the $SpO_2$ values on x-axis. For convenience, only a portion of two different sets of curves are displayed on FIG. 4. Midway between the high saturation alarm threshold (100% saturation) and low saturation alarm threshold (85% saturation), the curves switch from "probability of $SpO_2$ below value" curves at each accuracy to "probability of $SpO_2$ above value" curves at each accuracy. If all of the "below value" curves were displayed, they would start to level off and end at the point 100% probability/100% saturation. The "probability of $SpO_2$ above value" curves would be seen to continue to rise and then level off, approaching 100% probability to end at the point 100% probability/0% saturation. It should also be pointed out that at the $SpO_2$ value of 90% the probability curves converge.

This disclosure describes systems and methods for using accuracy and/or probability to reduce the number of nuisance alarms generated due to high noise in the data used to estimate physiological parameters. In an embodiment, the oximeter would adapt its alarm thresholds to assure that the probability of $SpO_2$ being outside the user-set limits was high before an alarm would be generated.

In order to illustrate this, consider the following three examples of estimated values of $SpO_2$ with different accuracies and probability distributions. The first example is a simple case in which no noise is measured and the sensor has a presumed accuracy ($SpO_2$–$SaO_2$) of +/−2% (1 standard deviation) due to physio-optics. Assuming that $SpO_2$–$SaO_2$ errors have a Gaussian zero-mean distribution, an $SpO_2$ of 85% really means that there is a 50% probability of $SaO_2$<85%, an 83% probability of $SaO_2$<87%, a 95% probability of $SaO_2$<88.3%, a 97.5% probability of $SaO_2$<89%, etc.

In the second example, there is noise in the data, perhaps due to motion artifact, and the current level of said noise corresponds to a somewhat degraded accuracy of +/−4% of oxygen saturation. In this situation, that same $SpO_2$ of 85% means that there is a 50% probability of $SaO_2$<85%, an 83% probability of $SaO_2$<89%, a 95% probability of $SaO_2$<91.6%, a 97.5% probability of $SaO_2$<93%, etc.

The third example is an extremely challenging case in which the accuracy is degraded to +/−8%, in which case an $SpO_2$ of 85% means that there is a 50% probability of $SaO_2$<85%, an 83% probability of $SaO_2$<93%, a 95% probability of $SaO_2$<98.2%, etc.

In embodiments described herein, different alarm thresholds are used to compensate for the different noise in order to reduce the instances of nuisance alarms due to noise. In an embodiment, this is done by designing the oximeter to alarm when the $SpO_2$, together with said noise metrics as indicated by the probability distribution, indicates a 95% probability that the $SaO_2$ is lower than 88.3% (set low saturation alarm threshold of 85 plus a 3.3% margin to reflect the probability distribution associated with a nominal 2% accuracy). In the first example above, the oximeter would alarm for estimated values of $SPO_2$<85%, but in the 2nd noisier example, it would alarm only for estimated values of $SpO_2$<81.7%, and in the third example this probability-enhanced oximeter would alarm only for estimated values of $SpO_2$<75.1%.

Figure 5:
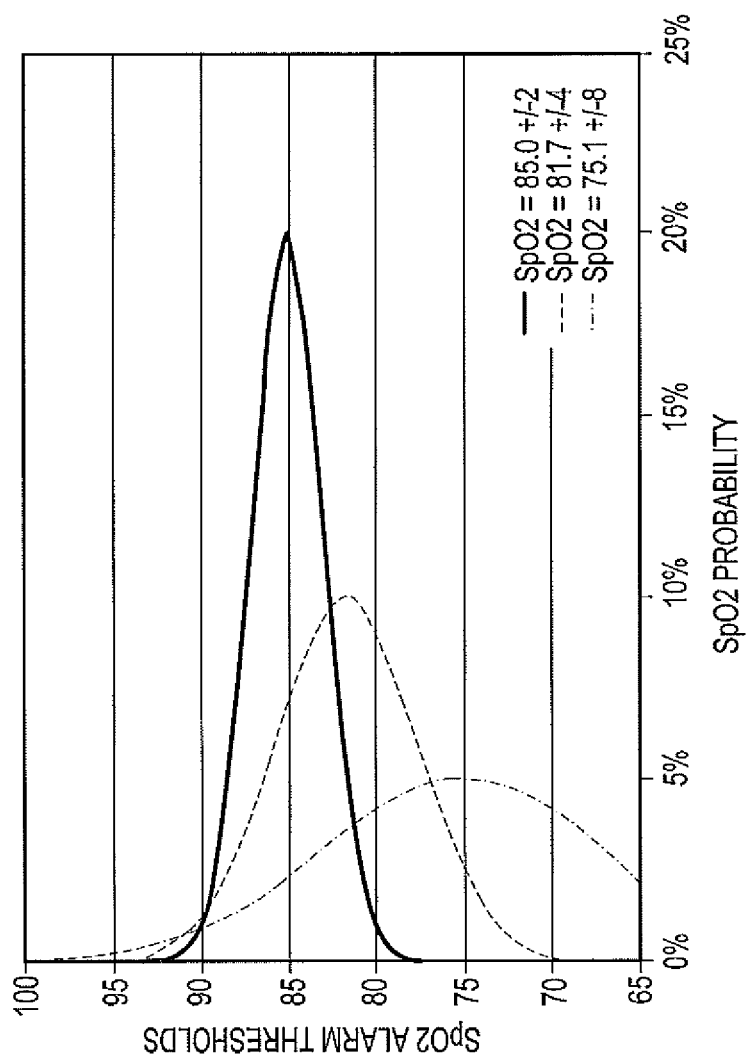
FIG. 5 illustrates the probability distributions of $SpO_2$ values equal to these alarm thresholds and associated $SpO_2$ accuracies (+/−1 standard deviation), according to an embodiment.

FIG. 5 illustrates the probability distributions of $SpO_2$ values equal to these alarm thresholds and associated $SpO_2$ accuracies (+/−1 standard deviation), according to an embodiment. In each case, the integral under the curve and above the $SpO_2$ alarm threshold of 88.3% (85%+3.3% margin) is 5%, although probability distributions differ substantially. This means that the probability that $SaO_2$ is NOT under this 88.3% threshold (probability of false alarm) is only 5% in each case. In contrast, if the low $SpO_2$ alarm limit were to remain fixed at 85%, then in the +/−8 case, an $SpO_2$ at this fixed limit of 85% would be associated with about a 40% probability of $SaO_2$≥88.3%, with a corresponding likelihood of false alarms.

In an alternative embodiment, at times when said noise metrics increase suddenly and dramatically, probability theory may be used to hold the older and presumably more accurate $SpO_2$ value, instead of displaying the newer but less accurate value, for some period of time determined based on the noise. For example, if an increase in said noise metrics indicates that $SpO_2$ accuracy has just degraded from +/−2 points to +/−8 points, the oximeter might be designed to hold the old $SpO_2$ value unless the new $SpO_2$ value has changed by 8 points or until the noise metrics go back down. Alternatively, it could assume that the accuracy of the held $SpO_2$ value might degrade at some fixed rate, such as for example 0.5% per second, and therefore hold the old $SpO_2$ value for no longer than 8.0/0.5=16 seconds.

Either the dynamic alarm threshold or holding scheme based on noise (signal quality) metrics in combination with probability significantly reduces nuisance alarms. Furthermore, a time-value integral may be used to reduce nuisance alarms. This method may integrate at a rate that was modified (reduced) by the probability that the estimated value exceeded the alarm threshold. It should be noted that, to the extent that the challenging conditions that degrade oximeter accuracy are brief in duration, modifying the oximeter's behavior to assure a higher probability that the alarms are real should preserve patient safety, as motion artifact generally biases $SpO_2$ low. Similarly, high $SpO_2$ alarms, to the extent that they are reduced or delayed in neonates, will be less urgent than low $SpO_2$ alarms, as they impact longer-term development rather than the body's ability to meet current metabolic demands.

Figure 6:
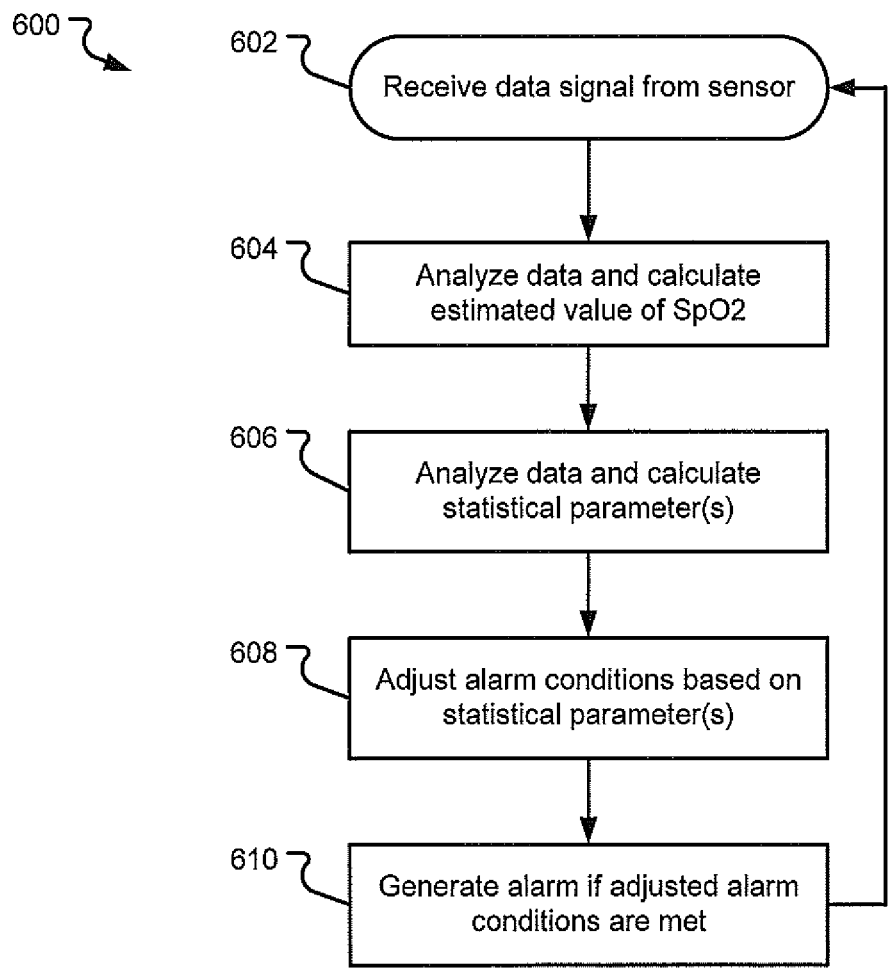
FIG. 6 illustrates an embodiment of a method for generating an alarm based on the monitoring of a physiological parameter, according to an embodiment.

FIG. 6 illustrates an embodiment of a method for generating an alarm based on the monitoring of a physiological parameter. In the embodiment shown, an alarm will be generated when the monitored physiological parameter is determined to meet an alarm condition. For the purposes of this disclosure, the alarm condition will be discussed in terms of a value of some parameter exceeding a threshold value. One skilled in the art will understand that when a value is said to "exceed a threshold" it means that the value is within a range of values for which an alarm should be generated; the range of values being separated by the threshold from an acceptable range of values for which an alarm will not be generated. Thus, the term "exceeding a threshold" covers both the instance in which a measured or calculated value is lower than a lower threshold of an acceptable range and the instance in which the measured or calculated value is higher that an upper threshold of the acceptable range.

In the method 600, information and/or data are received from a data source in a receive data operation 602. In the context of the pulse oximeter described above, the receive data operation 602 includes receiving an electronic signal from a sensor indicative of the light received by the detector and processing that signal to generate data that can be processed by the microprocessor. In an embodiment, the data, or samples thereof, may be temporarily stored in a buffer to allow multiple analyses of the same data. In additional, some or all of the data may be retained for some period of time for subsequent processing at a later time.

The received data are analyzed to generate an estimated value of the physiological parameter that is being measured in the generate estimate operation 604. In the context of a pulse oximeter, one physiological parameter estimated is the oxygen saturation of the blood of the patient. In an embodiment, the oxygen saturation of the patient's blood is calculated based on the most recent data received from the sensor in order to provide a current measurement of the oxygen saturation. The estimated value of the oxygen saturation may be generated by a sophisticated algorithm and may utilize a significant amount of processor cycles and signal processing hardware (e.g., filters, amplifiers, high-resolution digital to analog converters, etc.). In an embodiment, generation of the estimated value of the oxygen saturation may use statistical information derived from data in the generation of the final estimate. An example of generating an estimated value for oxygen saturation is described in the commonly-assigned U.S. Pat. No. 6,836,679, titled "Method and apparatus for estimating physiological parameters using model-based adaptive filtering". Other methods for generating the estimated value are known in the art and any suitable method, now known or later developed, may be used.

In addition to the generation of the estimated value, one or more statistical parameters describing the data are calculated in a calculate statistical parameters operation 606. In the embodiment shown, the calculate statistical parameters operation 606 is performed after the generate estimate operation 604. In alternative embodiments, the statistical parameter(s) may be calculated before, concurrently with or as part of the generate estimate operation 604. In yet another embodiment, the calculate statistical parameters operation 606 may be performed only if the estimated value exceeds a predetermined (i.e., non-adjusted) alarm condition.

Furthermore, the statistical parameter(s) calculated may or may not be used in the calculation of the estimated value and may or may not be calculated by the same module, software application or component of the pulse oximeter that calculates the estimated value. For example, in an embodiment, a single software application may be utilized to calculate all parameters. In an alternative embodiment, separate and independent software modules or system components may be used to calculate each parameter described herein.

One statistical parameter that may be determined from the data is a single value representing the accuracy of the estimated value. Accuracy is a well known statistical term of art referring how close an estimated value is likely to be to the actual value based on the errors and limitations of the measurement process and the data obtained. Accuracy can be quantified by many different techniques, including reporting a single value that is a numerical representation of the accuracy of the estimated value. For example, the accuracy of an estimated value of oxygen saturation may be determined by calculating a standard deviation of the physiological data from which the estimated value is determined; the smaller the standard deviation, the greater the accuracy of the estimated value. Thus, the standard deviation itself may be displayed as a parameter representing the accuracy of the estimated value.

In an alternative embodiment, the accuracy an estimated value may be further determined by more complicated calculations involving a detailed analysis of data received from the sensor. A number of data characteristics potentially indicative of the accuracy of pulse oximetry calculations (i.e. oxygen saturation and pulse rate) are know to those skilled in the art. Examples include pulse amplitude, pulse shape, correlation of the IR and Red photoplethysmograph, as well as temporal variations in any of these characteristics. Those skilled in the art of pulse oximeter design will also recognize that multiple data characteristics may be combined empirically in order to more accurately reflect the accuracy of a pulse oximetry system under challenging conditions that may be created experimentally or encountered in clinical usage. Those skilled in the art will also recognize that in order to design such an empirical combination, the accuracy of oxygen saturation and pulse rate measurements under challenging conditions may be independently assessed by techniques such as arterial blood sampling, ECG monitoring, or use of a second pulse oximeter at a different tissue site. Such empirical combinations of data characteristics reflective of the accuracy of a physiological parameter may involve linear or non-linear combinations, together with one or more thresholds, limits, coefficients, exponents, etc. The process of defining such an empirical combination of data characteristics, including gathering oximetry data representative of a variety of challenging conditions, may be time-consuming and complex, but would nevertheless be a routine undertaking for one of ordinary skill in the art.

Statistical parameters calculated in the calculate statistical parameters operation 606 may also include parameters based on probability distribution of the data. This may include selecting a probability profile (e.g., Gaussian) and matching the data to the profile in order to determine the statistical parameters.

An example of one such probability distribution statistical parameter is a confidence interval. A confidence interval is an interval estimate of a parameter. The confidence interval represents a range of values within which the actual value of the parameter is expected to occur with a high probability, referred to as the confidence level. For example, a confidence interval may be a range within which the actual value is expected to be with a 95% certainty. An alternative way of stating this is that there is a 95% probability that the actual value will be within the confidence interval.

When calculating confidence intervals, the confidence level to be used is identified as part of the operation 606. The confidence level may be predetermined by the system manufacturer, selected automatically by the system, or may be adjustable by the user of the system. For example, in an embodiment a system may use a 95% confidence level for all confidence interval calculations unless a user has specifically selected a different confidence level. The system may facilitate user selection of confidence levels by providing an interface, such as a confidence level selection menu, through which the user can select a confidence level (e.g., 90%, 95%, 97.5%, 98%, 99%, etc.) or enter a user-designated confidence level. Confidence levels received by the system from a user through such an interface may be stored in memory on the system and also may be displayed on the display GUI as described in greater detail below.

Confidence intervals may also be represented as confidence limits, such as an upper confidence limit and a lower confidence limit. A confidence limit is an interval estimate of a parameter indicating the probability that the actual value is above (or below) the limit. For the purposes of this disclosure, the terms "upper confidence limit" or "upper limit" refers to the upper limit of any confidence interval (including a confidence interval with no lower limit) and, likewise, the term "lower confidence limit" will be used when referring to the lower limit of any confidence interval with a lower limit. The relationship between the estimated value, its accuracy estimate, and its confidence interval depends on the probability distribution function of the measurement errors. Measurement errors are often presumed to have a Gaussian probability distribution, characterized by the "bell-curve" function $e^{-(x/\sigma)^2}$, where a denotes the standard deviation of the measurement errors (i.e. the accuracy). Assuming a Gaussian error distribution, an oxygen saturation estimate of 92% with an accuracy, σ, of 3% will have a 95% confidence interval of 92%±6%, or 86%-98%, because 95% of the area under the curve defined by a Gaussian error distribution falls within the range of ±2σ.

Confidence intervals, confidence limits and accuracy calculations are examples of statistical parameters that may be calculated by the method 600. The reader will understand that any other statistical parameter related to any aspect of the data (e.g., signal strength, noise, harmonics, etc.) may be calculated as part of the calculate statistical parameter operation 606.

After the calculations have been made, an alarm condition adjustment operation 608 is performed. In the alarm condition adjustment operation 608 an adjusted alarm condition is determined based on a predetermined alarm condition. In an embodiment, the predetermined alarm condition may be defined by a predetermined acceptable range that is defined by two predetermined thresholds. The predetermined thresholds may be user-selected thresholds or thresholds provided by the device manufacturer. The predetermined thresholds may be provided in terms of estimated value thresholds or in some other form, such as confidence limit thresholds.

The alarm condition adjustment operation 608 retrieves or otherwise accesses the predetermined alarm condition and then adjusts it, if necessary, based on the statistical parameters. In an embodiment, the predetermined alarm condition may be adjusted based on accuracy, probability distribution, or any other statistical parameter. The adjustment may include changing the value of a predetermined threshold (e.g., raising the threshold or lowering it), changing the type of threshold (e.g., changing a predetermined estimated value threshold to a threshold for a confidence limit) and/or changing a temporal condition (such as a delay period) that must be met in addition to some other condition such as the estimated value exceeding a threshold.

In the embodiment shown, the alarm condition adjustment operation 608 is illustrated as being performed after calculation of the estimated value and statistical parameters. In an alternative embodiment, the alarm condition adjustment operation 608 may be performed concurrently with or as part of the calculate statistical parameter(s) operation 606. In yet another embodiment, the alarm condition adjustment operation 608 may be performed only if the estimated value exceeds the non-adjusted alarm condition.

The alarm condition adjustment operation 608 may be omitted in an embodiment in which the predetermined threshold is defined in terms of a confidence level rather than in terms of an estimated value. For example, in an embodiment a predetermined threshold may be defined as a 95% confidence limit threshold of SaO2≥85% oxygen saturation. In this example, if the data indicate that there is 95% probability that the actual SaO2≥83%, the threshold is exceeded and the alarm should be generated. In this embodiment, the alarm is generated based on the predetermined threshold and the probability distribution without the need to adjust the alarm condition.

A generate alarm operation 610 is then performed in which the adjusted alarm condition is used to determine if an alarm should be generated (i.e., an audio alarm should be sounded, a visual alarm should displayed, an alarm notification should be sent, etc.). The generate alarm operation 610 includes testing the adjusted alarm condition against the current data and calculated values in order to determine if the adjusted alarm condition has been met. If the condition is met, an alarm is generated. An alarm may be generated until the measured data indicate that the adjusted alarm condition is no longer met, until a user resets the device, or until some other interrupt occurs.

In an embodiment, the adjusted alarm condition may include an adjusted threshold for a specific parameter (e.g., an accuracy, confidence interval, estimated value, etc.). The generate alarm operation 610 compares the adjusted threshold to the appropriate parameter to determine if the parameter exceeds the adjusted threshold (i.e., is outside of the acceptable range). If so, the alarm is generated. In an alternative embodiment, an adjusted alarm condition may include a temporal requirement (e.g., the estimated value must exceed the threshold for some period of time determined based on a statistical parameter) before the adjusted alarm condition is considered to be met. These and other embodiments of the adjusted alarm condition are discussed in greater detail below.

In an embodiment, the method 600 is performed continuously, which is illustrated by the flow returning to the receive data operation 602. That is, data is continually being received, calculations are made from the most recent data and the alarm conditions are continuously tested. Depending on the implementation, this can be done in a true continuous process or can be done by periodically repeating the operations in FIG. 6 for batches of data received and revising the displayed values after each repetition. For example, the method 600 may be performed twice every second.

Figure 7:
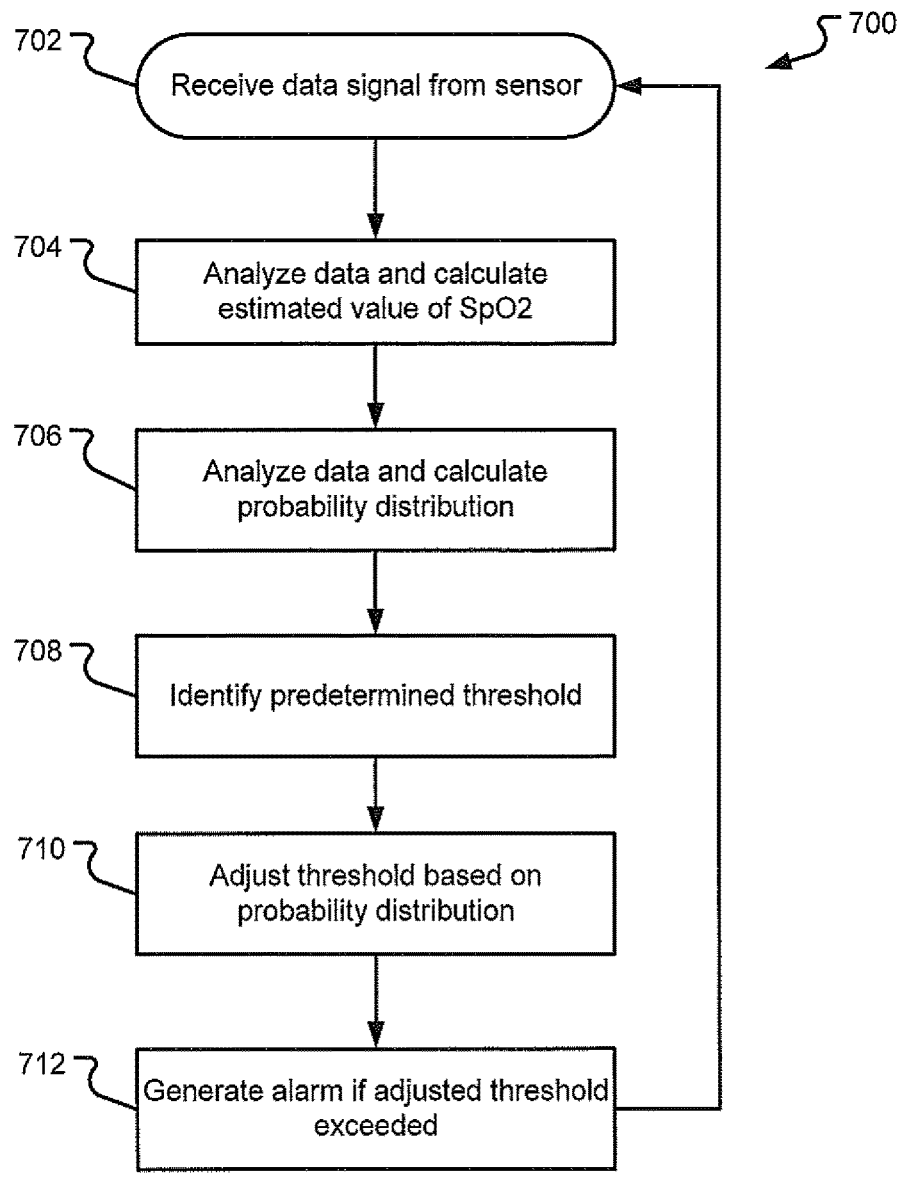
FIG. 7 illustrates an embodiment of a method for generating an alarm indicating that a physiological parameter has exceeded a predetermined threshold, according to an embodiment.

FIG. 7 illustrates an embodiment of a method for generating an alarm indicating that a physiological parameter has exceeded a predetermined threshold. In the embodiment shown, the method starts with the collection of data indicative of the physiological parameter from the patient in a data collection operation 702. In the context of a pulse oximeter, the data is received from a sensor and may take the form of a stream of data indicative of different light intensities measured by a detector as described above.

Next, a calculate estimated value operation 704 is performed. The estimated value of the physiological parameter being measured is calculated from the data received.

In addition, a calculate probability distribution operation 706 is performed. In an embodiment, this operation 706 calculates a probability distribution of the actual value of the physiological parameter based on the data received. As discussed above, the calculate distribution operation 706 may include calculating an accuracy of the estimated value. It may also include calculating a confidence interval or a confidence limit based on a predetermined confidence level, which may be retrieved from memory as part of the operation. The confidence level may be predetermined by the manufacturer (e.g., selected from 99%, 98%, 97.5%, 95%, 90%) or may be a user-selected value.

The calculate probability distribution operation 706 may be performed independently of the calculate estimated value operation 704 as illustrated. Alternatively, the two operations may be combined into a single operation. In addition, as discussed above the calculate probability distribution operation 706 may be performed automatically or only after a predetermined alarm condition has been met.

In the embodiment shown, a predetermined threshold is determined in an identify threshold operation 708. In the operation 708, a threshold may be retrieved from memory accessible by the system. This may include determining which predetermined threshold should be used based on other information such as patient characteristics, physiological parameter being monitored, etc.

A calculate adjusted threshold operation 710 is then performed. In the calculate adjusted threshold operation 710 the predetermined threshold is modified based on the probability distribution. In the embodiment shown, the predetermined threshold may be provided in terms of an estimated value threshold and the adjustment operation 710 includes calculating an adjusted estimated value threshold based on the probability distribution.

For example, in an embodiment the predetermined threshold may be a lower threshold limit of $SpO_2$=85% oxygen saturation. Due to an increased amount of noise (e.g., resulting an accuracy of +/−4 as described above) that changes the probability distribution of the estimated $SpO_2$ values, the predetermined threshold may be lowered to generate an adjusted threshold of $SpO_2$=81.7%. This results in an adjusted threshold for $SpO_2$ that maintains the ≤5% probability of a false alarm at the decreased accuracy.

A generate alarm operation 712 is then performed in which the adjusted threshold is used to determine if an alarm should be generated (i.e., an audio alarm should be sounded, a visual alarm should displayed, an alarm notification should be sent, etc.). The generate alarm operation 712 includes testing the adjusted threshold against the current data and calculated values in order to determine if the adjusted alarm condition has been met. If the threshold is exceeded, an alarm is generated.

As part of testing to determine if the adjusted alarm condition is met, the generate alarm operation 712 may compare the adjusted threshold to the appropriate parameter to determine if the parameter exceeds the adjusted threshold (i.e., is outside of the acceptable range). If so, the alarm is generated.

In an embodiment, the method 700 is performed continuously, which is illustrated by the flow returning to the receive data operation 702. That is, data is continually being received, calculations are made from the most recent data and the displayed values are continuously updated. Depending on the implementation, this can be done in a true continuous process or can be done by periodically repeating the operations in FIG. 7 for batches of data received and revising the displayed values after each repetition.

Figure 8:
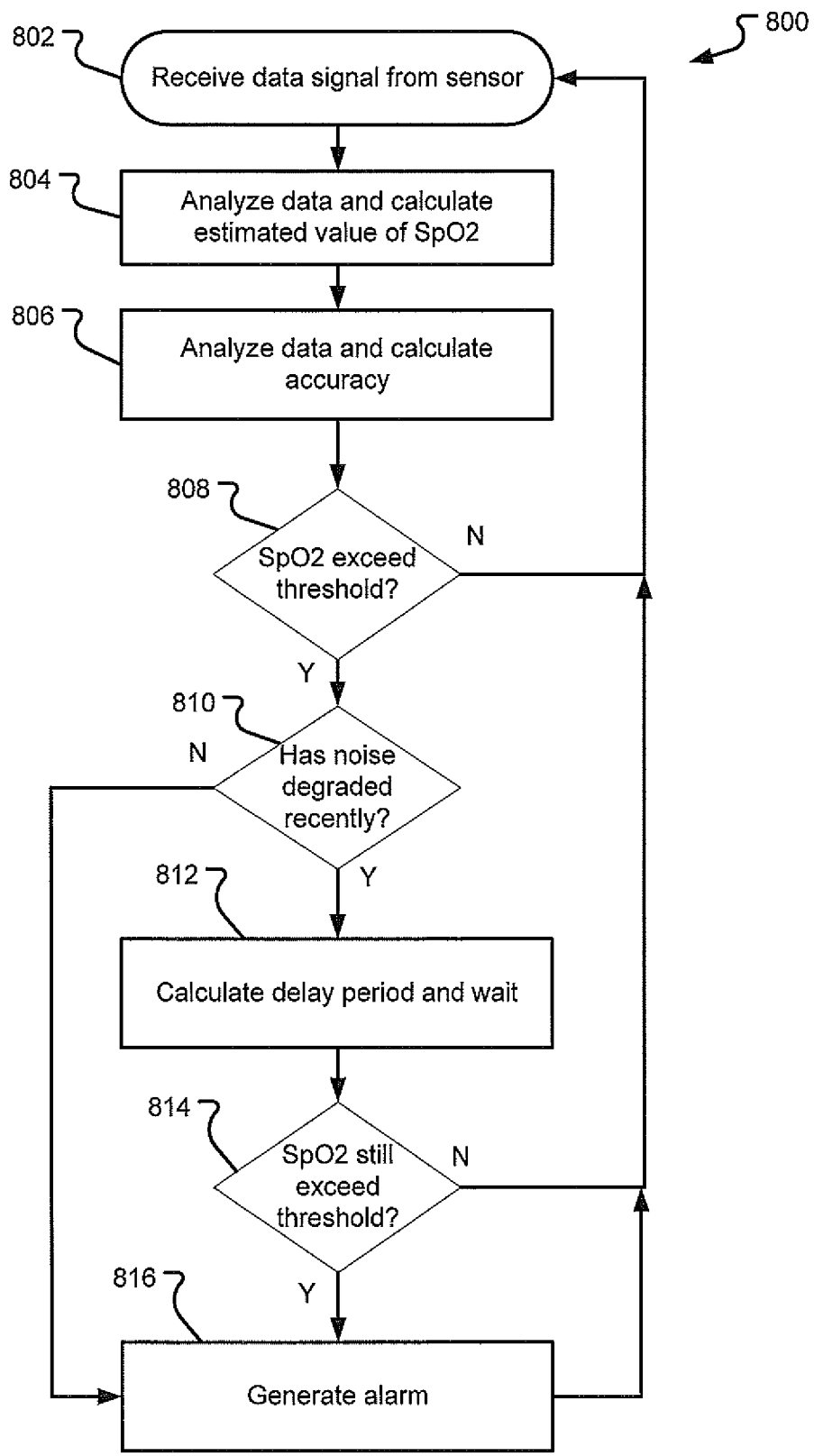
FIG. 8 illustrates an alternative embodiment of a method for generating an alarm indicating that a physiological parameter has exceeded a predetermined threshold, according to an embodiment.

FIG. 8 illustrates an alternative embodiment of a method for generating an alarm indicating that a physiological parameter has exceeded a predetermined threshold. In the embodiment shown, the method starts with the collection of data indicative of the physiological parameter from the patient in a data collection operation 802. In the context of a pulse oximeter, the data are received from a sensor and may take the form of a stream of data indicative of different light intensities measured by a detector as described above.

Next, a calculate estimated value operation 804 is performed. The estimated value of the physiological parameter being measured is calculated from the data received.

In addition, a calculate accuracy operation 806 is performed. In an embodiment, this operation 806 calculates the accuracy of the estimated value of the $SpO_2$ based on the data received. The calculate accuracy operation 806 may be performed independently of the calculate estimated value operation 804 as illustrated. Alternatively, the two operations may be combined into a single operation. In addition, as discussed above the calculate accuracy operation 806 may be performed automatically or only after a predetermined alarm condition has been met.

The method further performs a first determination operation 808 that determines if the predetermined alarm threshold has been exceeded. In the embodiment shown, this includes retrieving a predetermined $SpO_2$ threshold and comparing the threshold with the current estimated value of $SpO_2$. Alternatively, a different type of threshold (e.g., a confidence threshold or an adjusted threshold) may be retrieved as described above. If the threshold has not been exceeded, the normal monitoring and analysis continues as illustrated by the operational flow returning to the receive data operation 802.

If the threshold has been exceeded, then the accuracy is evaluated in a second determination operation 810. The purpose of the second determination operation 810 is to determine if the accuracy of the measurements and calculations being performed has recently degraded, thus indicating that the threshold may have been exceeded not because of a change in the physiological parameter but rather due to inaccurate estimation. In an embodiment, the second determination operation 810 compares the calculated accuracy of the current estimated value to one or more recently calculated accuracies. If there has not been a significant change between the current accuracy and the previous accuracy data (e.g., a difference of >+/−1% oxygen saturation, >+/−2%, >+/−3% or >+/−4% between the current and recent accuracies, for example), then the method 800 causes the alarm to be generated in a generate alarm operation 816. In order to facilitate this analysis, recent values of accuracies may be stored in temporary memory for the purpose of comparing them with accuracies calculated in the future. But if the accuracy has changed enough to meet the requirements of the second determination operation 810, a generate delay period operation 812 is performed.

In an alternative embodiment, the significance of the current accuracy may be based on a comparison with a predetermined acceptable accuracy range. This range may be determined by the manufacturer or selected by the user. For example, an acceptable range of +/−1%, +/−1.5% or +/−2% may be used as the predetermined acceptable range for accuracy within which any exceeding of the threshold will be automatically considered to be a true alarm condition. Thus, if the accuracy of the current estimate is +/−1.5% it would be considered to be within an acceptable range of, for example, +/−2% and the alarm is generated. If the accuracy is greater than the acceptable range, the generate delay period operation 812 may be performed.

In yet another embodiment, the second determination operation 810 may be omitted altogether. In this embodiment, any time a threshold is exceeded the method proceeds directly to the generate delay period operation 812 regardless of the accuracy of the current estimated value of the physiological parameter.

The generate delay period operation 812 identifies a delay period which is used to delay the generation of the alarm. One purpose of the delay period is to allow for the noise to subside and the accuracy to improve, in the event that the alarm is being triggered by noise and not actual changes in the measured physiological parameter. In another embodiment, a time-value integral may be used to reduce nuisance alarms and may integrate at a rate that is modified (reduced) by the probability that the estimated value exceeded the alarm threshold, such as described in U.S. Pat. No. 5,865,736.

In an embodiment, the delay period may be determined based on the calculated accuracy of the current estimate. Such a calculation may be based solely on the accuracy of the current estimate (as described above) or may be determined based on a comparison of the accuracy of the current estimate with the accuracy of one or more recent estimates. Alternatively, the delay period may be calculated based on a comparison of the accuracy of the current estimate with a predetermined accuracy or accuracy range, such as +/−2%. For example, in an embodiment a predetermined accuracy may be subtracted from the accuracy of the current estimate to determine an accuracy difference. This difference may then be used to calculate the delay period. For example, if the accuracy of the current estimate is +/−8% and the acceptable range is +/−2%, the difference may be calculated to be +/−6%. The difference may then be multiplied by some factor such as 2 seconds/% to determine the delay period (in this example, 12 seconds). Other algorithms are also possible and any mathematical algorithm for calculating a delay period based on an accuracy or a difference between accuracies may be used.

Alternatively, the delay period may be selected from one or more predetermined delay periods based on the calculated accuracy. For example, if a calculated accuracy is between the range +/−6% to +/−8%, then a predetermined delay period of 5 seconds may be used.

After waiting for the delay period, the method 800 illustrates a third determination operation 814 in which the alarm condition is tested again. The third determination operation 814 tests a newly estimated value and thus includes receiving additional data, calculating a new estimated value and, optionally, calculating a new accuracy. Thus, the third determination operation 814 could be considered to include repeating the receiving data operation 802, the calculate estimated value operation 804 and the calculate accuracy operation 806 as well as any operations (such as those shown in FIG. 7) necessary to determine and/or adjust the threshold.

If the third determination operation 814 determines that the threshold is no longer exceeded, the method returns to its normal monitoring state as illustrated by the operational flow returning to the receive data operation 802. On the other hand, if the third determination operation 814 determines that the threshold is still exceeded, a generate alarm operation 816 is performed.

In an alternative embodiment, the third determination operation 814 may be performed periodically during the delay period to determine if, during the delay period, the estimated value no longer exceeds the threshold or if the accuracy increases or decreases further. If in a determination operation 814 performed during the delay period it is determined that the estimated value no longer exceeds the threshold, then the method may return to its normal monitoring mode without generating an alarm. Alternatively, if the accuracy of the current estimates are determined to have degraded further, then the delay period may be recalculated in response.

The generate alarm operation 816 includes generating some form of notification, such as an audio alarm, a visual alarm, or an electronic message, that indicates that the threshold has been exceeded. As described above, an alarm may be generated until the measured data indicate that the adjusted alarm condition is no longer met, until a user resets the device, or until some other interrupt occurs.

As mentioned above, the methods described in FIGS. 7 and 8 could be combined to create yet another embodiment of a method for generating an alarm in which an adjusted threshold is calculated and if that threshold is exceeded, a delay period is used to delay the generation of an alarm.

Figure 9:
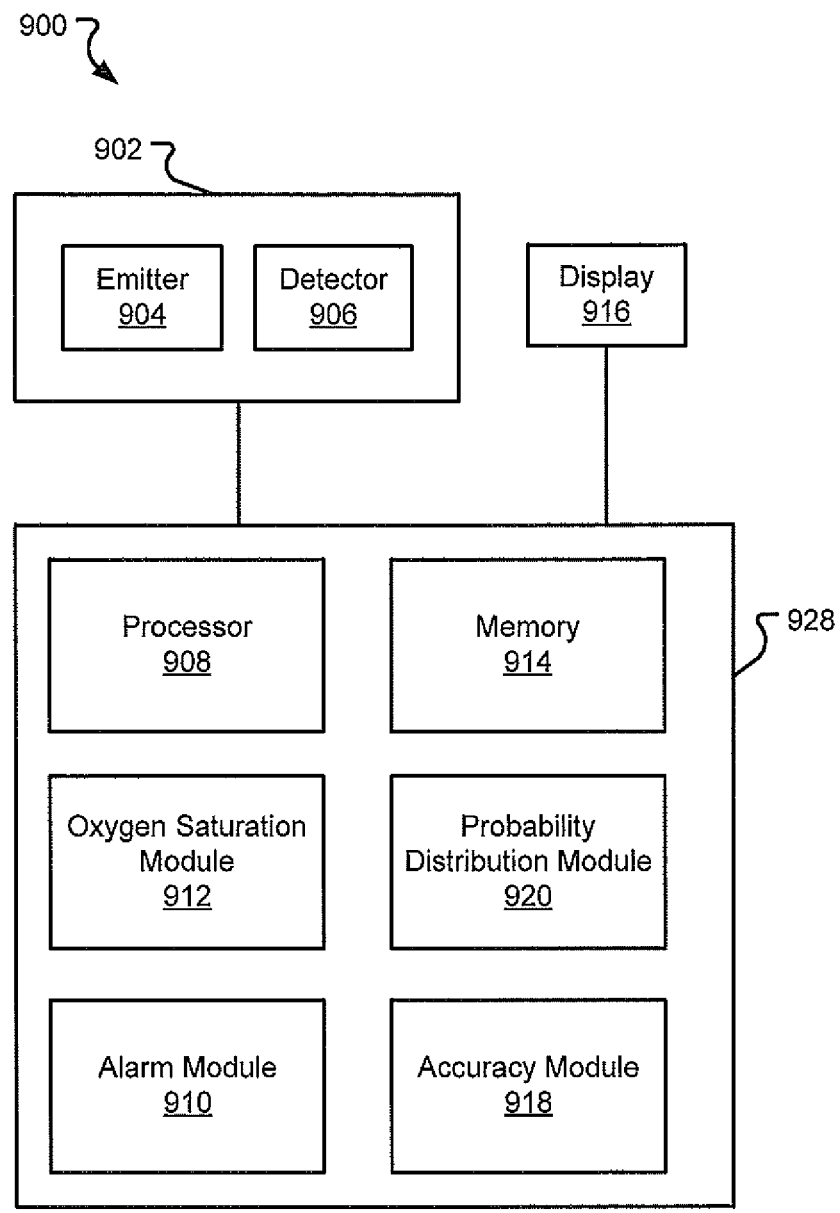
FIG. 9 is a block diagram illustrating some of the components of a pulse oximetry system that generates an alarm based the accuracy and/or probability distribution of sensed data, according to an embodiment.

FIG. 9 is a block diagram illustrating some of the components of a pulse oximetry system that generates an alarm based the accuracy and/or probability distribution of sensed data. In the embodiment shown, the system 900 includes a sensor 902 containing a light emitter 904 and a light detector 906; and, in a separate housing 918, a processor 908, an alarm module 910, a probability distribution module 920, an oxygen saturation module 912, an accuracy module 918 and a memory 914. A display 916 is also provided. The sensor 902 and its components operate as described previously with reference to FIG. 2.

The memory 914 may include RAM, flash memory or hard disk data storage devices. The memory stores data, which may be filtered or unfiltered data, received from the detector 906. The data may be decimated, compressed or otherwise modified prior to storing in the memory 914 in order to increase the time over which data may be retained. In addition, the memory 914 may also store one or more of the predetermined threshold, the adjusted threshold, at least one estimated value of oxygen saturation of a patient's blood, at least one accuracy associated with an estimated value, the probability distribution, and a delay time period calculated based on at least one accuracy of an estimated value.

The oxygen saturation module 912 generates a current oxygen saturation measurement from the data generated by the sensor. The probability distribution module 920 performs the analyses of the data received by the oximeter 918 and calculates the probability distribution for use in adjusting the alarm threshold. In an embodiment, the probability distribution module 920 is capable of calculating one or more parameters such as an upper confidence limit, a lower confidence limit, and a confidence interval based on information received from the sensor and a stored confidence level.

In the embodiment shown, a separate accuracy module 918 is illustrated. The accuracy module 918 is capable of calculating the accuracy of the estimated value of the oxygen saturation.

An alarm module 910 is further illustrated. The alarm module 910 tests the alarm condition and, if the conditions are met, generates an alarm as described above. The alarm module 910 is capable of generating an alarm based on the estimated value and a predetermined alarm threshold. In an embodiment, the alarm module is further capable of delaying the generation of an alarm based on the accuracy of the estimated value. In yet another embodiment, the alarm module is further capable of calculating an adjusted threshold based on the probability distribution and the predetermined threshold and then generating an alarm based on the adjusted threshold.

In an embodiment, the oxygen saturation module 912, alarm module 910, probability distribution module 920 and accuracy module 918 may each be a dedicated hardware circuit that may include filters, firmware comprising lookup tables or other data, and its own processor (not shown) that allow it to generate the current oxygen saturation measurement. In an alternative embodiment, they may be implemented as a single software application or separate software applications that are executed, in whole or in part, by the system processor 908. In yet another embodiment, functions described herein as being performed by the oxygen saturation engine and modules may be distributed among hardware, software and firmware throughout the system 900 and its other components.

The display 916 may be any device that is capable of generating an audible or visual notification. The display need not be integrated into the other components of the system 900 and could be a wireless device or even a monitor on a general purpose computing device (not shown) that receives email or other transmitted notifications from the oximeter 918.

It will be clear that the described systems and methods are well adapted to attain the ends and advantages mentioned as well as those inherent therein. Those skilled in the art will recognize that the methods and systems described within this specification may be implemented in many different manners and as such is not to be limited by the foregoing exemplified embodiments and examples. In other words, functional elements being performed by a single or multiple components, in various combinations of hardware and software, and individual functions can be distributed among software applications and even different hardware platforms. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the described technology. Numerous other changes may be made which will readily suggest themselves to those skilled in the art and which are encompassed in the spirit of the invention disclosed and as defined in the appended claims.

What is claimed is:

1. A method performed by a pulse oximeter comprising a processor and a memory, the method comprising:
    calculating an estimated value of an oxygen saturation of a patient's blood from information received from a sensor;
    calculating a probability distribution of an actual value of the oxygen saturation of the patient's blood based at least in part upon information received from the sensor;
    calculating, by the pulse oximeter, an adjusted threshold based at least in part upon the probability distribution and a predetermined threshold, wherein when the estimated value of oxygen saturation exceeds the adjusted threshold an alarm is indicated;
    determining that the estimated value of the oxygen saturation exceeds the adjusted threshold;
    determining, by the pulse oximeter, whether an accuracy of the estimated value has recently degraded by comparing a current accuracy of the estimated value to a previous accuracy of the estimated value; and
    delaying generating, by the pulse oximeter, the alarm based at least in part upon determining that the accuracy of the estimated value has recently degraded.

2. The method of claim 1, further comprising storing one or more of:
    the predetermined threshold,
    the adjusted threshold,
    the estimated value of the oxygen saturation of the patient's blood,
    the previous accuracy associated with the estimated value,
    the probability distribution, and
    a delay time period calculated based at least in part on the comparison of the current accuracy of the estimated value and the previous accuracy of the estimated value.

3. The method of claim 1, further comprising:
    calculating, based at least in part upon the probability distribution, a confidence interval for the actual value of the oxygen saturation of the patient's blood; and
    comparing the confidence interval to the predetermined threshold.

4. The method of claim 1, further comprising:
    retrieving a confidence level; and
    calculating, based at least in part upon the probability distribution, a confidence interval for the oxygen saturation of the patient's blood using the retrieved confidence level.

5. The method of claim 4, wherein the retrieved confidence level is selected from 99%, 98%, 97.5%, 95%, 90% and a user-selected value.

6. The method of claim 1, further comprising:
    calculating the current accuracy of the estimated value based at least in part upon the information received from the sensor.

7. The method of claim 6, wherein calculating the probability distribution further comprises:
    calculating the probability distribution of the actual value of the oxygen saturation of the patient's blood based at least in part upon the current accuracy of the estimated value.

* * * * *